United States Patent [19]

Lilius et al.

[11] Patent Number: 5,858,690
[45] Date of Patent: *Jan. 12, 1999

[54] METHOD FOR DETECTING ALLERGY

[75] Inventors: Esa-Matti Lilius, Kaarina; Erika Isolauri, Tampere; Seppo Salminen, Turku, all of Finland

[73] Assignee: Oy Aboatech Ab, Turku, Finland

[*] Notice: This patent issued on a continued prosecution application filed under 37 CFR 1.53(d), and is subject to the twenty year patent term provisions of 35 U.S.C. 154(a)(2).

[21] Appl. No.: 647,965

[22] PCT Filed: Apr. 12, 1996

[86] PCT No.: PCT/FI96/00199

§ 371 Date: May 30, 1996

§ 102(e) Date: May 30, 1996

[87] PCT Pub. No.: WO96/32645

PCT Pub. Date: Oct. 17, 1996

[30] Foreign Application Priority Data

Apr. 12, 1995 [FI] Finland ................................ 951778

[51] Int. Cl.⁶ .................................................. G01N 33/53
[52] U.S. Cl. ........................ 435/7.24; 435/7.1; 435/7.2; 435/7.8; 435/7.92; 435/7.94; 435/975; 436/513; 436/808; 436/811; 424/85.1; 424/85.2; 424/85.4; 424/85.5; 424/85.7; 424/805; 424/809; 424/810
[58] Field of Search .............................. 435/7.1, 7.2, 7.8, 435/7.92, 7.94, 7.24; 436/513, 811; 424/85.1, 85.2, 85.4, 85.5, 85.7, 805, 809, 810

[56] References Cited

U.S. PATENT DOCUMENTS

| | | | |
|---|---|---|---|
| 4,693,967 | 9/1987 | Gormus . | |
| 5,137,809 | 8/1992 | Loken et al. | 435/7.21 |
| 5,192,665 | 3/1993 | Salonen | 435/18 |
| 5,219,997 | 6/1993 | Schlossman et al. | 530/388.7 |
| 5,256,642 | 10/1993 | Fearon et al. . | |
| 5,409,901 | 4/1995 | Calabrese et al. | 514/21 |
| 5,487,977 | 1/1996 | De Weck | 435/7.24 |
| 5,547,669 | 8/1996 | Rogers et al. | 424/185.1 |
| 5,567,594 | 10/1996 | Calenoff | 435/7.32 |

FOREIGN PATENT DOCUMENTS

0629703A2  12/1994  European Pat. Off. ........ C12P 21/00

OTHER PUBLICATIONS

National Library of Medicine, File Medline, No. 85055468: Berger et al. "Human neutrophilis increase expression of C3bi as well as C3b receptors upon activation", *J. Clin Invest*, 1984, Nov; 74(5): pp. 1566–1571. (Abstract).

National Library of Medicine, File Medline, No. 95251993: Kindzelskii et al., "Imaging the spatial distribution of membrane receptors during neutrophil phagocytosis", *J Struct Biol* 1994 Nov–Dec; 113(3): pp. 191–198. (Abstract).

Suomalainen et al., Pediatric Research. vol. 32, No. 5, p. 611, 1992.

Suomalainen et al., Pediatric Allergy and Immunology. vol. 4, No. 4, pp. 203–207. (Abstract Only) 1993.

National Library of Medicine, File Medline, No. 93232613: Walker, Christoph et al. "Increased Expression of CD11b and Functional Changes in Eosinophils after Migration across Endothelial Cell Monolayers", *The Journal of Immunology*, vol. 150, pp. 4061–4071, May 1993. (Abstract & Article).

National Library of Medicine, File Medline, No. 94216648: Kroegel et al., "Blood and Bronchoalveolar eosinophils in allergic subjects after segmental antigen challenge: surface phenotype, density heterogeneity, and prostanoid production", *J Allergy Clin Immunol* 1994 Apr; 93(4): pp. 725–734. (Abstract).

National Library of Medicine, File Medline, No. 90170038: Hartnell et al., "Fc gamma and CD11/CD18 receptor expression on normal density and low density human eosinophils", *Immunology*, 1990 Feb; 69(s): pp. 264–270. (Abstract & Article).

National Library of Medicine, File Medline, No. 93299975: P:Erez–Arellano JL et al., "Comparison of two techniques (flow cytometry and alkaline immunophosphatase) in the evaluation of alveolar acrophage i mmunophenotype", *Daign Cytopathol*, 1993; 9(3): pp. 259–265. (Abstract).

*Current Opinion in Immunology*, vol. 5, 1993, Wolf H. Fridman, "Regulation of B–cell activation and antigen presentation by Fc receptors", pp. 355–360.

National Library of Medicine, File Medline, No. 93057057: Leino et al., "The up–and down–modulation of immunoglobulin G Fc receptors and complement receptors and activated human neutrophils depends on the nature of activator", *J Leukoc Bio*, 1992 Feb; 51(2): pp. 157–163. (Abstract).

Leino et al, Journal of Leukocyte Biology, vol. 51, pp. 157–163 (Feb. 1992).

Saito et al, JPN J ALLERGOL, 35(5) (1986)—Abstract Only.

*Primary Examiner*—Christopher L. Chin
*Assistant Examiner*—Bao-Thuy L. Nguyen
*Attorney, Agent, or Firm*—Birch, Stewart, Kolasch and Birch, LLP

[57] ABSTRACT

The present invention comprises a simple way of identifying the tendency towards allergy or allergy already broken out, and showing the probability of allergy in a patient, by measuring the receptor expression of the phagocytic cells of peripheral blood. With a logistic regression model a combination of variables were found which best describe the probability of allergy. Thus the invention relates to a method for detecting allergy and a test kit for accomplishing the method. The invention also relates to a sensitive and specific logistic model for determining the probability of allergy.

18 Claims, 2 Drawing Sheets

METHOD FOR DETECTING ALLERGY

FIELD OF THE INVENTION

The present invention comprises a simple way of identifying the tendency towards allergy or allergy already broken out, by measuring receptor expression of the phagocytic cells of peripheral blood. A combination of variables is also presented which best describe the probability of allergy. Thus the invention relates to a method for detecting allergy and a test kit for accomplishing the method, as well as to a method for determining the probability of allergy by using a logistic regression model.

BACKGROUND OF THE INVENTION

Allergic diseases are nowadays a very large problem of public health, and morbidity to allergy seems to be increasing. Food allergies are usually the first manifestation of allergy, and they are commonest in children under 3 years. After recedence of food allergy another allergic disease can later be developed in the patient.

The defence mechanisms of foreign substances are specific as e.g. antibody response, or non-specific as e.g. the defence reactions mediated through phagocytic inflammatory cells or complement and other proteins. The mechanisms have mutual regulation. Usually the primary phase comprises phagocytosis and the secondary phase the specific immune response. This is why measuring the parameters related to phagocytosis gives firsthand information of a possible sensitization which leads into allergy.

The as early as possible detection of the tendency towards allergy enables effective treatment of food allergy and preventive measures against other allergies.

In the diagnostics of allergy skin prick tests and determination of allergen specific IgE antibodies are generally used. However, these methods are useful only if the allergy is IgE-mediated, i.e. immediate or type I reaction. On the other hand the tests measuring the type I reaction are known to be unreliable in children under two years by whom allergy and especially food allergy is common and the IgE response develops slowly. Recent placebo-controlled predisposition tests carried out using double-blind techniques show that patients with food allergy can be divided into groups on the basis of the way of the reaction (skin, intestines, respiratory tract) and the time of the reaction (immediate and delayed reactions and intermediary forms thereof).

Especially in the diagnosis of food allergy with intestinal symptoms, and delayed food allergy (type III or type IV) the usefulness of the above mentioned methods is restricted, and distinguishing between allergic and other intestinal symptoms is especially difficult. The allergic inflammatory reaction caused by nutritives always causes changes in the intestinal mucous membrane, although the disease would show itself in e.g. skin. The early detection of the inflammatory changes has also importance for the prognosis of the patient.

Tendency towards allergy or allergy already broken out can be detected and monitored by measuring the expression of the receptors related to the phagocytosis of monocytes and neutrophils. The phagocytic cells have their own part in the origin of symptoms accompanied with allergy and especially food allergy. Phagocytic cells are able to release into the ambient tissue lytic enzymes and reactive forms of oxygen which are essential parts of the defence mechanism of the cell. Phagocytic cells receive their secreting signals through the receptors accompanied with phagocytosis. These receptors include FcγI, FcγII and FcγIII receptors for immunoglobulin G (IgG) and Complement receptor type 1 (CR1) and Complement receptor type 3 (CR3) receptors for derivates of C3, a component of the complement cascade. The expression level of these receptors effects the ability of phagocytes to secrete the compounds meant for the defence of the organism.

In in vitro tests it has been shown that immunologically activating compounds enable the two- or even threefold increase of the expression of complement receptors (Leino and Lilius, 1992, J. Leukocyte Biol., 51:157–163). In the same connection FcγRIII, which deviates from the other receptors mentioned in that it is not transmembraneous but attached on the surface of the cell by a glycosyl phosphatidyl inositol linkage (GPI), is easily detached, whereby its level is decreased into half. Further, it can be shown in vitro that cytokines, as gamma-interferon (IFNγ), cause a substantial FcγI-receptor expression in neutrophils. Monocytes have this receptor even normally. FcγII-receptor seems to be fairly stable and constitutive on the basis of in vitro tests. However, it has to be noted that receptor expression and the binding ability of the receptors are not always one and the same thing. The above mentioned receptors can be activated or deactivated without their amount changing. That is why it is important to determine also the function of the cells.

DESCRIPTION OF THE INVENTION

Figure 1:
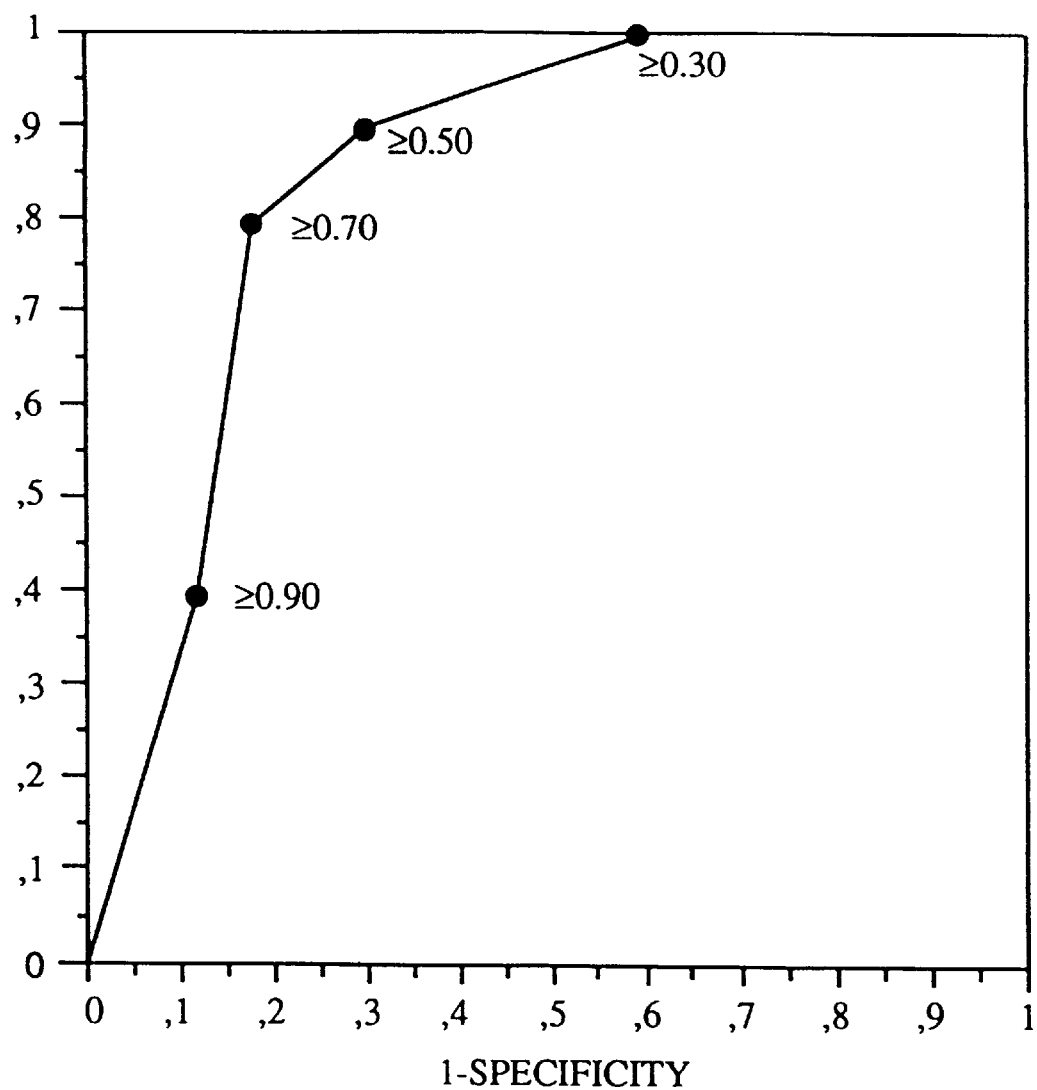
FIG. 1 Receiver operating characteristic (ROC) curve which shows the dependence of the indices of sensitivity and specificity on the selection of the cutoff point.

In the first series of experiments we studied the expression of the above mentioned receptors in child patients with atopic dermatitis, having food allergy in the background of the atopy. The values obtained were compared to the values of healthy children of the same age, and on the other hand child patients with an acute viral or bacterial infection. We noticed that in the patients with infection the expression of all receptors has elevated compared to the healthy children statistically significantly both in neutrophils and monocytes. According to these results it seems that by atopic children the densities of FcγRI and FcγRIII were decreased, but the density of FcγRII were increased in both neutrophils and monocytes compared to healthy children. However, these alterations are not statistically significant. The intensities of complement receptor s (CR1 and CR3) have increased.

On the basis of these observations it seems that the phagocytes of patients with allergy distinguish from the phagocytes of both healthy controls and those of the patients with an acute viral or bacterial infection, and patients with allergy can be screened out easily. By determining the expression of complement receptors patients with allergy can be distinguished from healthy individuals but not from patients with an infection, and by determining the expression of FcγRI, patients with allergy can be distinguished from patients with an infection.

The present invention thus relates on one hand to a method of detecting allergy in a patient, in which method CR1 and/or CR3 receptor expression of phagocytic cells is measured, and the values obtained are compared to the corresponding average values of healthy individuals, whereby the elevated expression values indicate the possible presence of allergy.

Additionally, the FcγI-receptor expression is measured to exclude infection. If the expression of this receptor is reduced compared to an infection control, the possibility of immune response caused by factors (as e.g. viruses or bacteria) other than allergic can be excluded.

If desired, the FcγIII receptor expression can also be measured in order to verify the result. The expression of this receptor seems also to be reduced in patients with allergy compared to the values obtained by patients with infection.

In the second series of experiments the same study population was used as in the first experiment supplementing the atopic patients' group with 12 more patients. The expression of said FcγI, FcγII, FcγIII, CR1 and CR3 receptors in neutrophils and monocytes was measured in a similar manner. With the results obtained in this series of experiments a stepwise binary logistic regression analysis was carried out to find a combination of variables which best describes the probability of allergy. As acute infections strongly affect receptor expression in both neutrophils and monocytes (as shown in the first series of experiments), to avoid diagnostic bias, children with acute infections were excluded from the analysis. Consequently, the results of logistic regression can be interpreted and applied only when simultaneous acute infection is excluded.

Stepwise binary logistic regression analysis of receptor variables showed significant and independent predictive effects for CR1 in neutrophils and FcγRI and FcγRII in monocytes (Table 1).

TABLE 1

Binary logistic regression of receptor variables of allergy. In the model CR1 is in neutrophils, and FcγRI and fcγRII are in monocytes.

| Receptor | Coefficient | SE | coefficient e | 95% CI |
|---|---|---|---|---|
| CR1 | 0.0415 | 0.017 | 1.04 | 1.01–1.08 |
| FcγRI | −0.0252 | 0.010 | 0.98 | 0.96–0.99 |
| FcγRII | 0.0334 | 0.013 | 1.03 | 1.01–1.06 |
| intercept | −4.40 | 1.76 | 0.012 | 0.0004–0.442 |

SE = standard deviation
CI = confidence interval

The regression equation thus took the form of:

$$\text{Probability of allergy} = \frac{1}{(-(-4.40 + 0.0415*CR1 - 0.0252*Fc\gamma RI + 0.0334*Fc\gamma RII))} 1 + e$$

where CR1 is in neutrophils, and FcγRI and FcγRII are in monocytes. The model yields continuous results between 0 and 1, and the indices of sensitivity and specifity depend on the selection of the cutoff point as depicted in the receiver operating characteristic (ROC) curve in FIG. 1. The sensitivity and specificity of the logistic model were higher compared to the univariate techniques. If the cutoff point and probability of 0.70 is used, the model has a specificity of 82% and a sensitivity of 80%.

Thus on the other hand the present invention relates to a method for determining the probability of allergy in a patient, which method comprises determining the CR1 receptor expression in neutrophils of a blood sample collected from the patient and determining the FcγI and FcγII receptor expressions in monocytes of said blood sample, comparing the values obtained with those of healthy individuals, the elevated CR1 receptor expression on neutrophils and reduced FcγRI/FcγRII ratio in monocytes showing the probability of allergy. The probability of allergy can also be calculated using the regression equation given above.

The receptor assays according to the methods of this invention are carried out e.g. using an immuno reaction with an antibody specific to each receptor using flow cytometric analysis.

The method according to the invention is in general carried out by isolating phagocytic cells from a blood sample drawn from a patient, and measuring the expression of said receptors in them. The phagocytic cells can be isolated by osmotic lysis of erythrocytes of the blood sample by adding e.g. $NH_4Cl$, and washing the debris of the lysed erythrocytes and plasma out of the blood sample, whereby only leukocytes will be left. The amount of different leukocyte types (neutrophils, monocytes) can be measured directly with e.g. flow cytometry.

To measure the receptor expression the isolated leukocytes are labelled in cold (ca 4°5° C.) with a monoclonal antibody specific to the receptor in question. The antibody is fluorescence labelled, or it will be labelled with a secondary fluorescence labelled antibody after being attached onto the surface of the cell. The fluorescence intensity of each cell type is measured by flow cytometry. From the results the amount of each cell type is obtained, one pulse corresponding to one cell, and the amount of the receptor to be measured, as well as the percentage of the cells in which the receptor is present.

However, flow cytometric receptor expression studies are relatively expensive and time-consuming, whereas luminometric assays are cheap and rapid. At best a luminometric assay can be effected of finger tip blood using a simple luminometer, the use of which does not demand noticeable laboratory expertise. This kind of method enables the screening of allergic patients e.g. in child health centres.

Thus the receptor expression measurements can also be carried out luminometrically, whereby the leukocytes isolated as described above are labelled with the same monoclonal antibodies as in flow cytometry, but now luminescence labelled, whereby the amount of receptors is obtained luminometrically as the magnitude on the luminescence signal (mV).

A luminometric receptor expression assay is p referably carried out as follows: Isolated leukocytes (neutrophils or monocytes) are first labelled with a primary monoclonal antibody specific to the receptor to be measured. The mixture obtained is washed with a suitable buffer, and then it is incubated with a secondary antibody attached to an enzyme conjugate. A substrate to the enzyme conjugate is added into the mixture, and the luminometric intensity is measured. All cells to which the antibody is attached give a light signal.

A preferable enzyme conjugate for the present luminometric assay is alkaline phosphatase, which is easy to use, and for which as table substrate solution is available.

In addition, to decrease the mV-response of the cell background the alkaline phosphatase of the leukocytes can be eliminated with a blocker.

Figure 2:
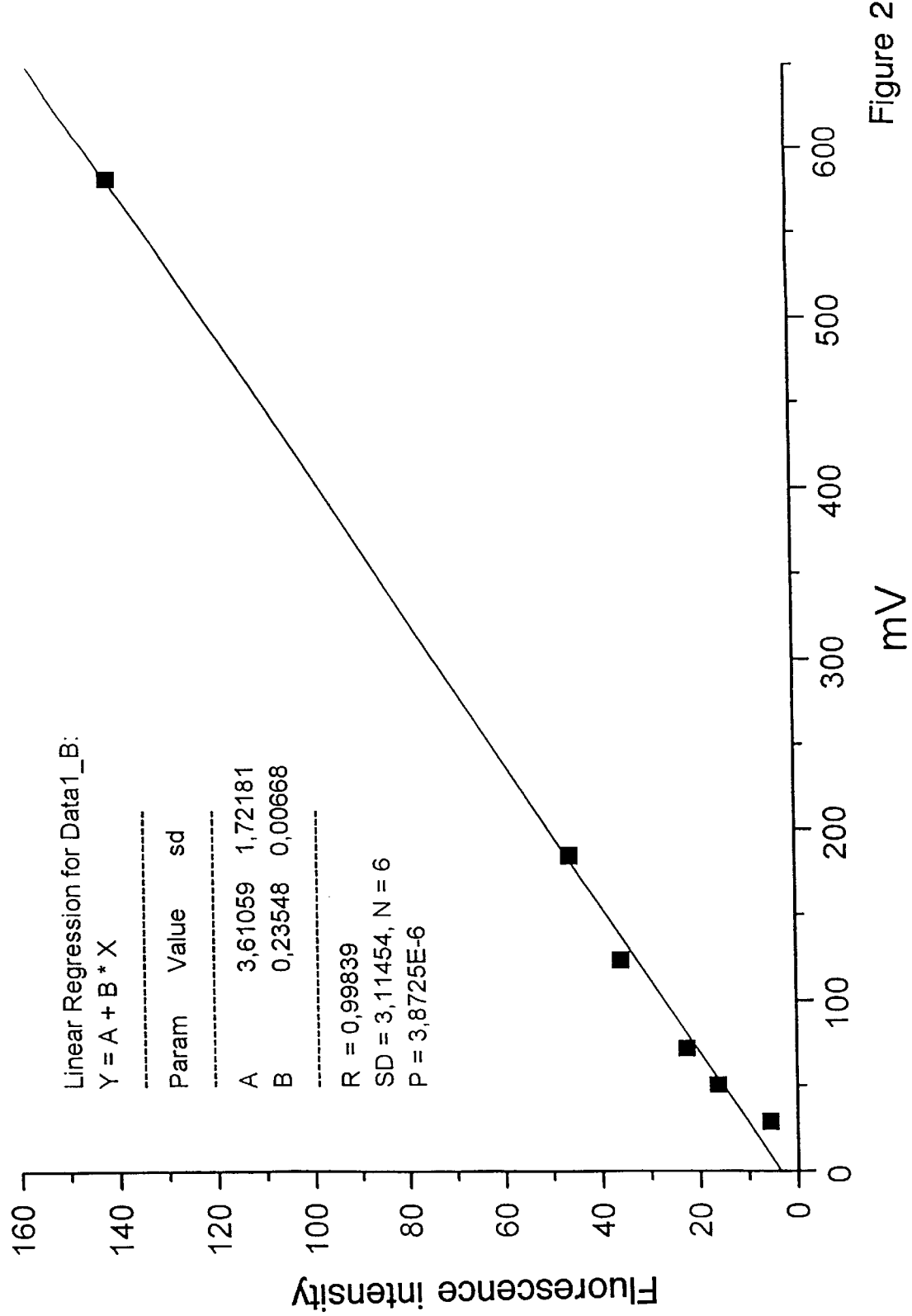
FIG. 2 Comparison of flow cytometric (fluorescent intensity) and luminometric measurements (mV); fluorescence intensity vs. magnitude of the luminescence signal in millivolts (mV).

We have compared the flow cytometric and luminometric receptor assays in neutrophils using linear regression analysis, and the results obtained show good correspondence (FIG. 2.)

The present invention relates further to a test kit for carrying out the methods according to the invention, the test kit comprising means for determining the expression of said receptors either by flow cytometry or luminometry.

For flow cytometric assay the test kit comprises antibodies specific to the receptors to be determined, a fluorescence label, and buffers necessary in the assay.

For luminometric assay the test kit comprises primary antibodies specific to the receptors to be determined, secondary antibodies with an enzyme conjugate, a substrate to the enzyme conjugate, and buffers necessary in the assay.

In the following the preferred embodiments of the invention are described. Two series of experiments were carried out, and the results obtained in said experiments are given. A specific example of carrying out the luminometric assay is also given, as well as the comparative data of luminometric vs. flow cytometric assays.

Experiment I

Study population

The study population comprised children aged 0 to 3 years being treated at Tampere University Hospital. The first control group comprised 17 children who had no infections or symptoms indicating allergy, and they were thus considered to form the healthy controls in respect of this study (group A). The second control group consisted of 17 children, who had an acute infection in upper respiratory tract or another acute viral or bacterial infection, and they were thus considered to form the infection control group in this study (group B). The sick study subject group comprised 27 patients with atopic dermatitis and in the background thereof food allergy (group C).

Collection and preparation of blood samples Venous blood samples were collected both from control and test subjects in test tubes without EDTA. In the blood coagulated during transport erythrocytes were lysed with 0.83% ammonium chloride for 10 min at room temperature, and centrifuged (400×g, 10 min, 4° C.). The leukocyte pellet was suspended in ice cold $Ca^{2+}$- and $Mg^{2+}$-free Hank's balanced salt solution (CMF-HBSS) and kept on ice until used in the receptor studies.

Measurement of receptor expression The expression of CR1, CR3, FcγI, FcγII and FcγIII receptors in neutrophils and monocytes were measured by flow cytometry as described by Leino and Lilius (supra). Briefly, aliquots of leukocyte suspension were labelled with anti-CR1, anti-CR3 (Becton-Dickinson, Mountain View, Calif.), anti-FcγRI, anti-FcγRII and anti-FcγRIII (Medarex Inc., West Lebanon, N.H., U.S.A.) monoclonal antibodies for 30 min at 4° C. The control samples were labelled with monoclonal antibodies risen against irrelevant antigens. Flow cytometric analysis was performed with a FACScan (Becton-Dickinson) flow cytometer. The laser excitation wavelength was 488 nm and the fluorescence of fluorescein isothiocyanate (FITC) was measured at 520 nm and that of phycoerythrine (PE) (anti-CR3-antibody) at 580 nm. The fluorescence of 5000 cells was measured, about 4500 of which were neutrophils and about 500 monocytes.

Statistics

ANOVA + the test for paired values were used in comparing the differences in the values of the patient and control groups. P<0.05 was considered significant.

Results

In Table 2. the values obtained by flow cytometry are given (fluorescence intensity) for each receptor in neutrophils, and in Table 3. in monocytes. The values mean average amounts of receptors per cell or the percentage (%) of the cells where the receptor is expressed, respectively.

TABLE 2

The average amount (fluorescence intensity) or percentage (%) of CR1, CR3, FcγI, FcγII and FcγIII receptors in neutrophils in healthy controls (A), controls with infection (B) and atopic patients (C). p = statistical significance.

| Receptor | A ± sd | B ± sd | C ± sd | p (A,B) | p (B,C) | p (A,C) |
|---|---|---|---|---|---|---|
| CR1 | 60 ± 21 | 86 ± 39 | 82 ± 20 | 0.01992 | 0.62815 | 0.00259 |
| CR3 | 589 ± 262 | 758 ± 264 | 842 ± 227 | 0.08059 | 0.28898 | 0.00174 |
| FcγRI (%) | 46 ± 30 | 80 ± 28 | 45 ± 25 | 0.00178 | 0.0001 | 0.84854 |
| FcγRI intensit. | 27 ± 16 | 55 ± 41 | 21 ± 10 | 0.0118 | 0.00029 | 0.19124 |
| FcγRII | 126 ± 25 | 218 ± 71 | 143 ± 26 | 0.00003 | 0.00002 | 0.04377 |
| FcγRIII intensit. | 883 ± 284 | 925 ± 314 | 690 ± 209 | 0.68303 | 0.00519 | 0.1421 |

TABLE 3

Average amount (fluorescence intensity) or percentage (%) of CR1, CR3, FcγI, FcγII and FcγIII receptors of monocytes in healthy controls (A), controls with infection (B) and atopic patients (C). p = statistical significance.

| Receptor | A ± sd | B ± sd | C ± sd | p (A,B) | p (B,C) | p (A,C) |
|---|---|---|---|---|---|---|
| CR1 | 76 ± 29 | 96 ± 30 | 97 ± 22 | 0.05728 | 0.87861 | 0.01198 |
| CR3 | 717 ± 380 | 1008 ± 442 | 952 ± 211 | 0.05443 | 0.585 | 0.01271 |
| FcγRI intensit. | 102 ± 56 | 159 ± 80 | 85 ± 35 | 0.02265 | 0.00021 | 0.23057 |
| FcγRII | 129 ± 40 | 213 ± 88 | 162 ± 29 | 0.00125 | 0.0099 | 0.00444 |
| FcγRIII (%) | 31 ± 19 | 42 ± 17 | 42 ± 14 | 0.07247 | 0.99068 | 0.031 |
| FcγRIII intensit. | 158 ± 134 | 198 ± 97 | 132 ± 71 | 0.40888 | 0.02368 | 0.39837 |

Experiment II

Study subjects and design

Study subjects were partly the same children as in the Experiment I. To the atopic dermatitis group 12 objects were added. Three groups of children aged 1 to 55 months, mean 14 months, were studied with their parents' consent: (1) 39 atopic dermatitis patients, (2) 17 age-matched patients with an acute infection, and (3) 17 age-matched healthy children. The study was approved by the Ethical Committee of Tampere University Hospital.

The atopic dermatitis group comprised 39 children aged 1 to 55 (mean age 11 months) fulfilling the Hanifin criteria (Hanifin, J. M., 1987, Monogr. Allergy, 21:116–131) for atopic eczema in children. They had been referred to a pediatric clinic on the basis of suspected food allergy and were allocated to double-blind placebo controlled or open cow milk challenge as described previously (Isolauri, E. and Turjanmaa, K., 1996, J. Allergy Clin. Immunol., 97:9–15). The inclusion criteria for the study was that the patient be free of symptoms and signs of acute infection and had not received any medication during the previous month. None of the patients was receiving systemic corticosteroid therapy. Blood samples for the receptor studies were collected at the presentation.

The second group included patients, aged 1 to 37 (mean age 16) months, who were admitted for acute respiratory infections or acute gastroenteritis, septicaemia or urinary tract infection. Blood samples were collected during the first 12 hours in hospital.

The third group comprised children, aged 1 to 38 (mean age 16) months, who were studied as outpatients for minor operations or previous investigations. All were found healthy. The criteria for enrollment were no acute infections for the previous month and no history of atopy or food allergy in the family.

Collection and preparation of blood samples

Peripheral, EDTA-anticoagulated (1.5 mg EDTA/1 ml of blood) blood samples were collected from the study subjects. Blood erythrocytes were lysed with 0.83% ammonium chloride at 20° C. for 15 min. After lysation leukocytes were centrifuged (400×g for 10 min at 4° C.) and resuspended in ice-cold CMF-HBSS.

Measurements of receptor expression

Leukocytes ($3 \times 10^5$) were incubated with monoclonal antibodies in 12×75 mm polystyrene vials for 30 min at +4° C. Incubation volume was 90 μl. Control sample was incubated with isotype matched monoclonal antibodies directed to irrelevant antigen. After incubation cells were washed with cold CMF-HBSS. Leukocytes were resuspended in 500 μl of cold CMF-HBSS and they were ready to flow cytometry examination.

Flow cytometry

Flow cytometric analysis was performed with FACScan (Becton Dickinson, Mountain View, Calif., USA) flow cytometry with an argon ion laser. The laser excitation wavelength was 488 nm. Emitted light was collected through a 560 nm and 600 nm dichromic filter and through 530 nm and 585 nm bandpass filters. The fluorescence of 5000 cells was measured using logarithmic amplification. A relative measure of receptor expression was obtained by determining the mean log fluorescence intensity. The percentage of positive cells was generally 98–100 unless otherwise indicated.

Statistics

The data in Tables 4 and 5 are given as medians with lower and upper quartiles. The Kruskal-Wallis test with paired contrasts was used for comparing differences between groups. Level of significance was <0.05. A stepwise logistic regression analysis was done to identify the best combination of receptors for detecting atopic dermatitis and food allergy. The probability of atopic sensitization estimated by the logistic model was then used as a new diagnostic variable. A child with the estimated probability higher than the specific cutoff points can be estimated and classified as allergic. The indices of sensitivity and specificity for positive and negative test results were calculated using the receiver operating characteristic (ROC) curve (see FIG. 1).

Results

With the second larger group of patients we could substantially confirm the results as regards the receptor expressions obtained in the first experiment. However, it was established that in fact in allergic patients none of the receptor expressions were significally reduced compared to those of healthy individuals. This finding deviates somewhat from the results obtained in the first experiment.

The children with acute infections had on the average higher receptor expression in both neutrophils (Table 4) and monocytes (Table 5) compared to healthy controls. With the exception of the frequency of CR3 in neutrophils, and CR1 and CR3 in monocytes, and FcγRIII in neutrophils and monocytes the differences were statistically significant.

The patients with atopic dermatitis had higher complement receptor CR1 expression compared to healthy controls. By contrast, the frequency of receptors for IgG was indistinguishable from that in healthy controls (Tables 4 and 5). The expression of FcγRI and FcγRII in neutrophils and in monocytes, and FcγRIII in monocytes was significantly lower in patients with atopic dermatitis and food allergy than those with acute infections (Tables 4 and 5).

Using a logistic regression model we could show (see the regression equation above), that the combination of variables which best describes the probability of allergy, is CR1 in neutrophils and FcγRI and FcγRII in monocytes. It thus seems, that in atopic sensitization, as determined in this study by a logistic regression analysis, the distinctive pattern of receptor expression is elevated CR1 on neutrophils and reduced FcγRI/FcγRII ratio in monocytes.

The results obtained in these experiments suggest that a distinct receptor profile of phagocytic cells can be characterized in atopic dermatitis patients with food allergy, providing a new direction to the search for early identification of children predisposed to allergic sensitization.

TABLE 4

Fcγ and CR receptor expression of neutrophils, median (lower quartile-upper quartile), in healthy controls, disease control patients with acute infections, and in children with atopic dermatitis and food allergy.

| Receptor | Healthy controls (n = 17) | Infection controls (n = 17) | Atopic dermatitis (n = 39) | Kruskal-Wallis test |
|---|---|---|---|---|
| CR1 | 63 (38–78) | 87 (54–114) | 87 (61–101) | p = 0.008 |
| CR3 | 680 (300–844) | 772 (580–982) | 780 (468–1003) | p = 0.12 |
| FcγRI | 21 (15–37) | 42 (23–74) | 22 (15–26) | p = 0.006 |
| FcγRII | 124 (107–147) | 222 (157–266) | 144 (112–160) | p = <0.0001 |
| FcγRIII | 842 (725–990) | 850 (705–1098) | 630 (524–874) | p = 0.03 |

TABLE 5

Fcγ and CR receptor expression of monocytes, median (lower quartile-upper quartile), in healthy controls, disease control patients with acute infections, and in children with atopic dermatitis and food allergy.

| Receptor | Healthy controls (n = 17) | Infection controls (n = 17) | Atopic dermatitis (n = 39) | Kruskal-Wallis test |
|---|---|---|---|---|
| CR1 | 71 (60–91) | 92 (68–104) | 85 (77–101) | p = 0.12 |
| CR3 | 737 (300–1038) | 1003 (709–1272) | 813 (501–1028) | p = 0.19 |
| FcγRI | 86 (68–138) | 133 (103–194) | 72 (57–113) | p = 0.0006 |
| FcγRII | 139 (97–152) | 203 (165–226) | 147 (126–185) | p = 0.0005 |
| FcγRIII | 114 (89–148) | 197 (120–253) | 113 (93–164) | p = 0.04 |

Luminometric assay and comparison thereof with flow cytometric assay

CR1, CR3, FcγRI, FcγRII and FcγRIII receptor expressions in isolated neutrophils were measured by luminometry as follows.

Neutrophils ($3 \times 10^5$) were incubated with 0.5 μg of primary monoclonal antibodies (CD35 for CR1: CLB, Amsterdam, Holland; CD11b for CR3, CD64 for FcγRI, CD32 for FcγRII and CD16 for FcγRIII: PharMingen, San Diego, Calif., USA) in polystyrene vials for 30 min at 4° C. Incubation volume was 50 μl. After incubation the cells were washed with 500 μl of cold CMF-HBSS (containing 0.1% Na-azide). The cells were incubated on ice for 30 min with secondary antibodies (AP-F(ab')$_2$ Rabbit anti-mouse IgG (H+L), Zymed, San Francisco, Calif., USA) conjugated to alkaline phosphatase (AF). The mixture was then washed three times with CMF-HBSS buffer as above, and the substrate solution (AMPPD, Tropix, Bedford, Mass., USA) was added. While AMPPD is degraded by alkaline phosphatase, light measurable by luminometry is emitted. The amount of the light is proportional to the amount of the enzyme and thereby to the amount of the primary antibody attached to the receptor. A blocker (Levamisole solution, Zymed) was used to eliminate the alkaline phosphatase included in the cells. LKB Wallac 1251 luminometer (Turku, Finland) was used.

To compare the results on the luminometric assay to the flow cytometric assay, a flow cytometric assay was carried out using the same unlabelled monoclonal anti-receptor antibodies than in the luminometric assay. The antibodies were detected on the cell wall using a FITC-labelled secondary antibody (FITC-Goat anti-mouse IgG (H+L), Zymed). Fluorescence intensities were measured as described in the paragraph "Flow cytometry" above.

The comparative results are given in Table 6.

TABLE 6

Comparison of luminometric (LM) and flow cytometric (FC) assays.

| Receptor | Receptor amount* | FC(FI) | LM(mV) | A |
|---|---|---|---|---|
| CR1 | 7000–40000 | 16.3 | 50.2 | 10000 |
| CR3 | 17000–65000 | 35.9 | 123.6 | 25000 |
| FcγRI | <1000 | 5.6 | 28.6 | 5700 |
| FcγRII | 10000–60000 | 46.2 | 184.7 | 37000 |
| FcγRIII | 100000–300000 | 140.5 | 583.4 | 120000 |

*number of receptors per cell, values given in literature
A number of receptors as calculated on the basis of the number of cells used in the luminometric assay, matching well with the literature values
FI = fluorescence intensity
mV = millivolts Background: Cells+anti-mouse-FITC: intensity 2.1
Cells+anti-mouse-AF: 12.6 mV Comparison of the two assay methods by linear regression analysis showed that the luminometric assay gives results comparable to those obtained in flow cytometric assay (FIG. 2).

We claim:

1. A method for detecting allergy comprising:
   (a) collecting a blood sample from a patient;
   (b) determining in the blood sample complement receptor 1 (CR1) and/or complement receptor 3 (CR3) expression of phagocytic cells;
   (c) further determining FcγI receptor expression in said cells;
   (d) comparing the CR1 and/or CR3 receptor expression values obtained to corresponding average values of healthy individuals; and
   (e) comparing the FcγI receptor expression value obtained to corresponding average values of patients with an acute viral or bacterial infection, wherein elevated CR1 and CR3 values and a reduced FcγI receptor expression value indicate the presence of allergy.

2. The method according to claim 1 wherein FcγIII receptor expression on phagocytic cells is also determined and a reduced FcγIII receptor expression indicates the presence of allergy.

3. The method according to claim 2 wherein the CR1, CR3 and FcγI expressions are determined by immunoreaction with antibodies specific to each of the receptor.

4. The method according to claim 3 wherein the CR1, CR3 and FcγI receptor expressions are determined fluorimetrically.

5. The method according to claim 3 wherein the CR1, CR3 and FcγI receptor expressions are determined luminometrically.

6. The method according to claim 4, further comprising, prior to step b)
   a1) separating leukocytes from erythrocytes and plasma in said sample;
   a2) labeling said leukocytes with fluorescence labeled monoclonal antibodies specific to each of the receptors to be measured; and wherein step c) further comprises,
   determining in neutrophils, CR1 and CR3 receptor expression, and in monocytes FcγI receptor expression by flow cytometry by measuring a fluorescence intensity thereof.

7. The method according to claim 5 further comprising, prior to step b)
   a1) separating leukocytes from erythrocytes and plasma in said sample;
   a2) labeling said leukocytes in a solution with primary monoclonal antibodies specific to CR1, CR3 and FcγI receptors;
   a3) incubating the labeled leukocytes with secondary antibodies which bind said primary antibodies conjugated to an enzyme;
   a4) adding into the solution a substrate of the enzyme; and wherein step c) further comprises,
   determining from the leukocytes the expression of said receptors by luminometry by measuring a luminescence intensity thereof.

8. A method for determining a probability of allergy in a patient which has been sensitized to an antigen, comprising:
   a) determining CR1 receptor expression in neutrophils of a blood sample collected from the patient;
   b) determining FcγI and FcγII receptor expressions in monocytes of said blood sample; and
   c) comparing values obtained for the expression of CR1, FcγI and FcγI receptors with those of healthy individuals, wherein an elevated CR1 receptor expression on neutrophils and a reduced FcγI/FcγII receptor expression ratio in monocytes indicate the probability of allergy.

9. The method according to claim 8, wherein the probability of allergy is further calculated using a regression equation as follows:

$$\text{Probability of allergy} = {}_{1+e}(-(-4.40+0.0415 \cdot CR1 - 0.0252 \cdot Fc\gamma I + 0.0334 \cdot Fc\gamma II)}{[1+e]}^{1}$$

10. The method according to claim 8, wherein the receptor expressions are determined by flow cytometry.

11. The method according to claim 8, wherein the receptor expressions are determined by luminometry.

12. A method for detecting allergy in a patient having at least one symptom of allergy, comprising:
   a) determining the CR1 receptor expression in neutrophils of a blood sample collected from the patient;

b) determining the FcγI and FcγII receptor expressions in monocytes of said blood sample; and c) comparing the values obtained with those of healthy individuals, an elevated CR1 receptor expression on neutrophils and a reduced FcγI/FcγII receptor expression ratio in monocytes indicates the existence of allergy.

13. The method according to claim 12, wherein the existence of allergy is further calculated using a regression equation as follows:

$$Probability\ of\ allergy = _{1+e}(-(-4.40+0.415 \cdot CR1 - 0.0252 \cdot Fc\gamma I + 0.0334 \cdot Fc\gamma II)_{[1+e]}{}^{-1}$$

wherein CR1 is in neutrophils, and FcγI and FcγII are in monocytes.

14. A test kit for carrying out the method according to claim 1, comprising antibodies consisting of antibodies specific to CR1 and/or CR3 receptors and antibodies specific to FcγI receptor, a fluorescence label for said antibodies and buffers necessary for a flow cytometric assay.

15. A test kit for carrying out the method according to claim 1, comprising primary antibodies consisting of primary antibodies specific to receptors consisting of CR1, CR3 and FcγI receptors, a secondary antibody which recognizes said primary antibodies, said secondary antibody being conjugated to an enzyme label, a substrate, and buffers necessary in a luminometric assay.

16. A test kit for carrying out the method according to claim 10, comprising antibodies consisting of antibodies specific to CR1-, FcγI- and FcγII-receptors, a fluorescence label for said antibodies and buffers necessary in a flow cytometric assay.

17. A test kit for carrying out the method according to claim 11, comprising primary antibodies consisting of primary antibodies specific to CR1-, FcγI- and FcγII-receptors, a secondary antibody which recognizes said primary antibodies, said secondary antibody being conjugated to an enzyme label, a substrate, and buffers necessary in a luminometric assay.

18. A test kit for carrying out the method according to claim 1, comprising primary antibodies consisting of primary antibodies specific to receptors comprising CR1, CR3 and FcγI receptors, a secondary antibody which recognizes said primary antibodies, said secondary antibody being conjugated to an enzyme label, a substrate, and buffers necessary in a luminometric assay.

* * * * *

UNITED STATES PATENT AND TRADEMARK OFFICE
CERTIFICATE OF CORRECTION

PATENT NO. : 5,858,690
DATED : January 12, 1999
INVENTOR(S) : Esa-Matti LILIUS et al.

It is certified that error appears in the above-indentified patent and that said Letters Patent is hereby corrected as shown below:

Column 3, lines 48-50, replace

" $\text{Probability of allergy} = \dfrac{1}{(-(-4.40+0.0415*CR1-0.0252*Fc\gamma RI+0.0334*Fc\gamma RII))} 1+e$ "

with

--Probability of allergy=
[1+e(exp)(-(-4.40+0.0415*CR1-0.0252*FcγRI+0.0334*FcγRII))]$^{-1}$ --

Signed and Sealed this

Thirtieth Day of November, 1999

Attest:

Q. TODD DICKINSON

Attesting Officer

Acting Commissioner of Patents and Trademarks